(12) United States Patent
Spector

(10) Patent No.: US 8,419,668 B2
(45) Date of Patent: Apr. 16, 2013

(54) COMPACT PACKAGE FOR AN ORTHOPEDIC CAST

(76) Inventor: Donald Spector, New York, NY (US)

( * ) Notice: Subject to any disclaimer, the term of this patent is extended or adjusted under 35 U.S.C. 154(b) by 189 days.

(21) Appl. No.: 12/752,568

(22) Filed: Apr. 1, 2010

(65) Prior Publication Data

US 2011/0245745 A1   Oct. 6, 2011

Related U.S. Application Data

(60) Provisional application No. 61/310,332, filed on Mar. 4, 2010.

(51) Int. Cl.
*A61F 5/00* (2006.01)

(52) U.S. Cl.
USPC ................................... 602/8; 602/6

(58) Field of Classification Search .......... 602/8, 6
See application file for complete search history.

(56) References Cited

U.S. PATENT DOCUMENTS

| | | | |
|---|---|---|---|
| 4,131,114 A | 12/1978 | Kirkpatrick et al. | |
| 4,241,007 A | 12/1980 | Tanaka et al. | |
| 4,273,115 A | 6/1981 | Holland et al. | |
| 4,376,438 A | 3/1983 | Straube et al. | |
| 4,411,262 A | 10/1983 | von Bonin et al. | |
| 4,433,680 A | 2/1984 | Yoon | |
| 4,454,873 A | 6/1984 | Laufenberg et al. | |
| 4,502,479 A | 3/1985 | Garwood et al. | |
| 4,841,958 A * | 6/1989 | Ersfeld et al. ............ 602/8 |
| 4,984,566 A | 1/1991 | Sekine et al. | |
| 5,005,566 A | 4/1991 | Klintworth, Jr. | |
| 5,172,629 A | 12/1992 | Merry | |
| 5,277,954 A | 1/1994 | Carpenter et al. | |
| 5,370,927 A | 12/1994 | Scholz et al. | |
| 5,449,550 A | 9/1995 | Yasis et al. | |
| 5,474,522 A | 12/1995 | Scholz et al. | |
| 5,807,292 A | 9/1998 | Delmore | |
| 5,997,492 A | 12/1999 | Delmore et al. | |
| 6,063,980 A * | 5/2000 | Peterson et al. ............ 602/49 |
| 2007/0073201 A1 | 3/2007 | Campagna et al. | |

* cited by examiner

*Primary Examiner* — Patricia Bianco
*Assistant Examiner* — Camtu Nguyen
(74) *Attorney, Agent, or Firm* — Collard & Roe, P.C.

(57) ABSTRACT

A compact package for making an orthopedic cast is disclosed. The package comprises a fabric folded and compressed, having an initial over-all surface area, that, when saturated with water, expands to final over-all surface area that is larger by a factor greater than 50 than the initial over-all surface area. The expansion of the fabric occurs during a first time period. The package also includes a water-curable material, impregnated into the fabric, so that when the material is saturated with water, the material cures over a second period of time to become rigid, wherein the second period of time is substantially longer than the first period of time. When the package is used, the fabric impregnated with the material may be immersed in water and expanded. Once expanded and unfolded, the fabric may be placed around a portion of a body for which the orthopedic cast is desired. When the second time period elapses, the material has become rigid so as to form the orthopedic cast.

12 Claims, 6 Drawing Sheets

COMPACT PACKAGE FOR AN ORTHOPEDIC CAST

CROSS REFERENCE TO A RELATED APPLICATION

This application claims priority under 35 U.S.C. §119(e) of U.S. provisional application 61/310,332 filed on Mar. 4, 2010 by Donald Spector, the applicant.

TECHNICAL FIELD

The present invention relates to orthopedic casts, and more particularly to compact packages that can be used in forming an orthopedic cast.

BACKGROUND ART

It is known in the prior art to make an orthopedic cast from fabric material that is placed onto a limb of a patient that has either a broken bone or a sprained joint. The fabric material cures over the limb of the patient and forms an orthopedic cast. Many different types of orthopedic casting materials have been developed including ones that use plaster of Paris in combination with cotton gauze that when immersed in water allows the fabric to be conformed to the patient's limb and which hardens as the water evaporates. In addition to plaster of Paris, other casting materials include polyisocyanate prepolymers such as polyurethane resin or fiberglass fibers that are impregnated into fabrics.

In battlefield conditions, emergency settings, and at sporting events, broken bones or sprained joints are generally stabilized using splints or wraps, since casting materials are not carried in medic kits due to size and usability constraints. Splints and wraps do not adequately stabilize the bone or joint and tend to slip as the limb is moved. Thus, the limb or joint may be undergo additional trauma during transport.

SUMMARY OF THE INVENTION

In a first embodiment of the invention there is provided a compact package for making an orthopedic cast. The package comprises a fabric folded and compressed, having an initial over-all surface area, that, when saturated with water, expands to final over-all surface area that is larger by a factor greater than 50 than the initial over-all surface area. The expansion of the fabric occurs during a first time period. The package also includes a water-curable material, impregnated into the fabric, so that when the material is saturated with water, the material cures over a second period of time to become rigid, wherein the second period of time is substantially longer than the first period of time. When the package is used, the fabric impregnated with the material may be immersed in water and expanded. Once expanded and unfolded, the fabric may be placed around a portion of a body for which the orthopedic cast is desired. When the second time period elapses, the material has become rigid so as to form the orthopedic cast.

In embodiments of the invention, the fabric may be formed from non-woven fibers, such as non-woven cotton fibers. In other embodiments of the invention, the non-woven fabric is viscose. The water-curable material may include urethane links In certain embodiments the water-curable material is a polyurethane resin. The water-curable material may include polyisocyanate prepolymers. The water-curable material is activated by the presence of water and a catalyst.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Various embodiments of the invention provide a package for making an orthopedic cast that is extremely compact. The compact size makes the package practical as a common emergency supply item for use on the field in sports, for use in industrial environments having substantial risk of personal injury, and for military use on the battlefield.

Various embodiments of the invention provide a fabric that is subject to extreme compression before being deployed to make the cast. The fabric may be decompressed by immersion in water. Typically the fabric is folded before compression, and therefore, after being decompressed, the fabric is unfolded. Techniques for making such a compressed fabric are described in U.S. Pat. No. 4,241,007, for an invention of Tanaka, which is hereby incorporated herein by reference. Tanaka discloses suitable fabrics including non-woven binderless cellulosic fabric. U.S. Pat. No. 5,172,629 to Merry describes compressed woven fabrics and is incorporated herein by reference.

Embodiments of the invention utilize such a fabric subjected to extreme compression while also impregnating the fabric with a water-curable material. The material must become rigid following immersion in water. For successful implementation of embodiments of the invention, it is required that the curing time for the material to become rigid must be greater than the amount of time required to expand the compressed cloth in water, to unfold it, and to position it on the area of the body for which a cast is desired.

One important design parameter for the water curable material is its cure time. Another design parameter is the physical properties of the material. The material must be able to make the fabric rigid after curing while, before curing, the composition must be capable of residing in interstices of the fabric in a manner without unduly inhibiting extreme compression of the fabric. Furthermore, the material must exhibit suitable physical stability in the cure process, and desirably, for use in making of an orthopedic cast, avoid undue shrinkage or expansion in the cure process. In addition, the material must be otherwise compatible with the fabric and not react with the fabric so as to interfere with the manner of use described herein. It is believed that suitable materials may include those disclosed in U.S. Pat. Nos. 4,131,114, 4,376,438, 4,411,262, 4,433,680, and 4,502,479 all of which are incorporated herein by reference in their entirety.

Figure 1A:
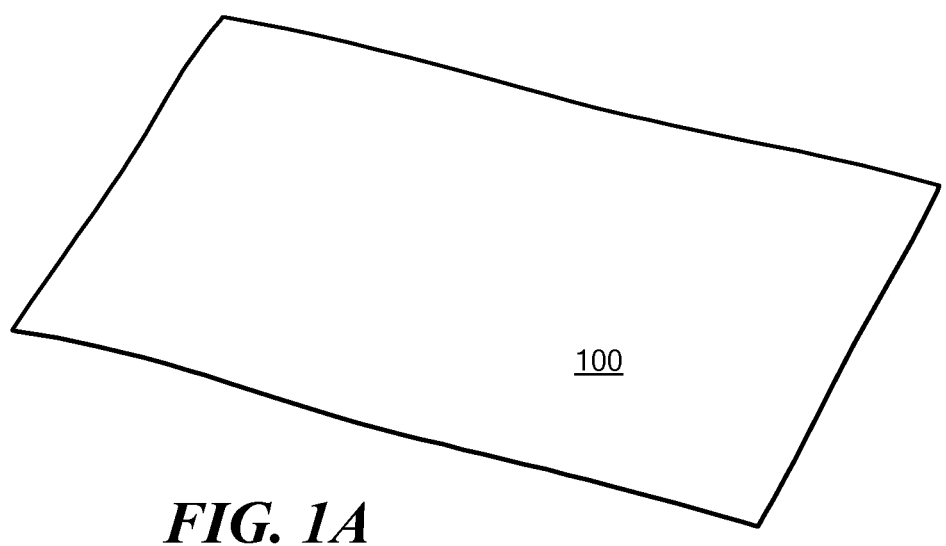
FIG. 1A shows a fabric prior to being compressed forming a sheet.

FIG. 1A shows a fabric 100 forming a sheet prior to being compressed in accordance with an embodiment of the invention. In one embodiment, the fabric 100 is made from non-woven fibers. The non-woven fibers may be spun lace and can be made from cotton or other natural or man-made material. For example, the fabric 100 may be made from viscose. In other embodiments, the fabric is a woven fabric. The fabric should be hydrophilic and may be manufactured from cotton, polyester, polyamides, such as nylon, acrylic, rayon, polyolefins treated to be hydrophilic. The fabric may be a composite composed of multiple fabrics or a blend formed into non-woven knit, woven or melt blown fiber construction. In order for the fabric to be compressed, the fabric should have a relatively low modulus of elasticity. Preferably the fabric is porous so that the fabric can be at least partially impregnated with a water-curable material. The structure of the fabric should be such that the interstices and apertures provide enough volume for the loading of the resin while still having significant volume for compressibility. Additionally, the fabric should be extensible when saturated with water such that the material can be form-fitted and conform to the body part on which the fabric is being applied as a cast.

Preferably, the fabric 100 is a sheet sized to be large enough to be wrapped around a limb (arm, leg) or portion (neck) of a patient. The sizing of the fabric in sheet size is preferable, since the sheet can readily cover an area of a limb without having to significantly move the limb of the patient causing additional trauma. Multiple sheets may be used to form a cast. For example, a first sheet may be placed on a surface and the limb placed on the sheet. The sheet can then be manipulated and conformed to the limb. A second sheet can be placed on top of the limb and the two sheets can be overlapped to fully wrap the limb. In contrast to large sheet-sized fabric, a tape-sized fabric may be preferable for use when creating a cast about the hand and wrist area of an injured patient. Tape-sized fabric may be rectangularly shaped with varying lengths and with widths of about 4-6 cm in preferred embodiments.

Figure 1B:
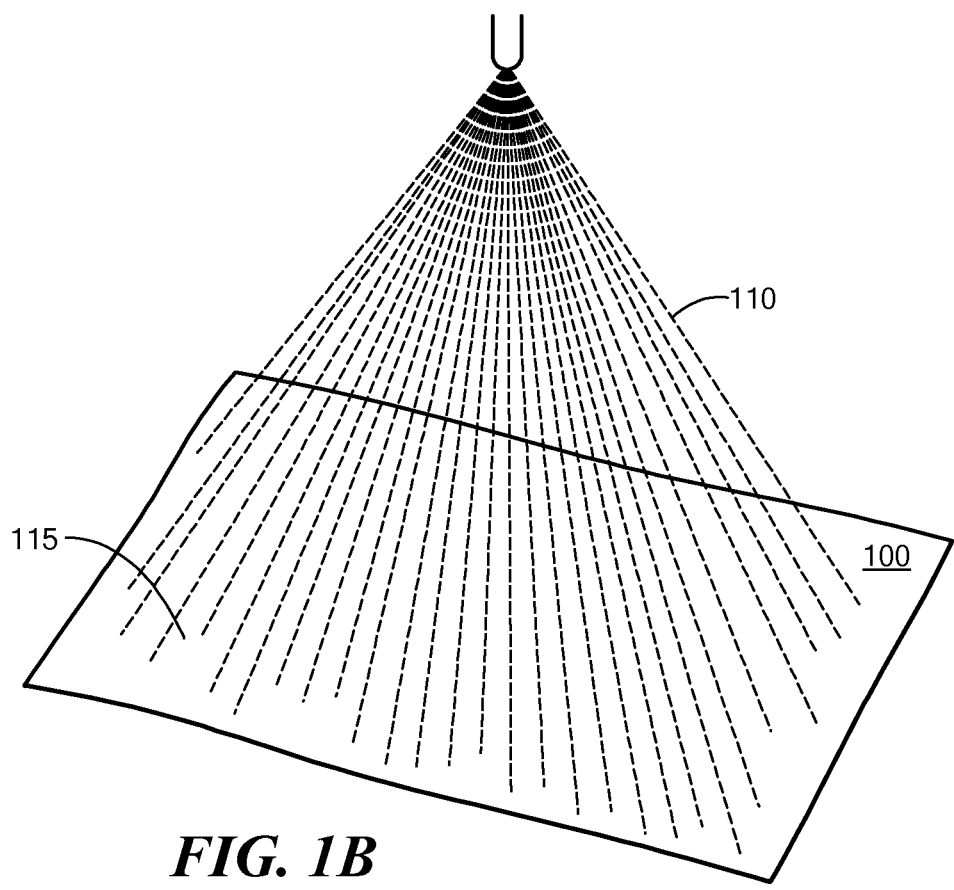
FIG. 1B shows the fabric being impregnated with a water-curable material.

FIG. 1B shows the fabric 100 being impregnated or coated with a water-curable material 110. The fabric 100 may include a water-curable material 110 that includes isocyanate that reacts with the water in the presence of a catalyst. A water-curable isocyanate-functional prepolymer is derived from polyisocynate compound and a reactive hydrogen compound or oligomer such as a polyol. The fabric sheet 100 can be impregnated or coated with a water-curable material 110, such as, a polyurethane resin that includes a curing catalyst. Polyurethane polymers are formed through step-growth polymerization by reacting a monomer containing at least two isocyanate functional groups with another monomer containing at least two alcohol groups along with a catalyst. The polyurethane can be made in a variety of densities and hardnesses by varying the type of monomers used. Once cured the fabric sheet should exhibit hardness characteristic of an orthopedic cast, such that the cured material has an immobilizing stiffness. Preferably, the cast should be of such a stiffness that it can be loaded with weight. In an uncured state, the fabric sheet 100 that has been impregnated with the water-curable material 110 must exhibit physical characteristics permitting the material to be substantially compressed, so that the surface area changes between the uncompressed state and the compressed state by a factor on the order of 50 or greater. The amount of polyurethane resin (water-curable material) that is applied to the fabric may be determined based upon the desired rigidity and the desired compressibility of the fabric-resin combination. It should be recognized that water-curable materials have been used with both high and low modulus of elasticity fabrics (See U.S. Pat. Nos. 5,370,927 and 4,984,566 respectively), and that both natural fabrics (U.S. Pat. No. 4,273,115) and synthetic fabrics (U.S. Pat. No. 5,474,522) also have been used with water-curable materials. Each of the foregoing referenced patents is incorporated herein by reference.

U.S. Pat. No. 5,370,927 teaches that the amount of resin applied to the fabric will amount to approximately 35 to 50% by weight of the fabric and resin combination. One possible resin, such as the Echelon-branded polyurethane prepolymer, produced by Dow Chemical, has a density of approximately 1 $gm/cm^3$. As an example, the fabric may be non-woven cotton having an area of 30 cm×30 cm. The cotton may be selected to have a thickness of 0.8 mm. The fabric may have an approximate density of 0.0625 $gm/cm^3$ and will weigh approximately 4.5 gm. The fabric may be impregnated with approximately 2 gm of resin. Given the resin's density of 1 $gm/cm^3$, the resin distributed over the surface of the fabric will have a thickness of approximately 0.2 mm, or about one quarter of the thickness of the fabric.

The water-curable material 110 is preferably sprayed on to the fabric 100 so that the water-curable material coats the fibers of the fabric and enters the interstices 115. Care needs to be taken to provide uniform distribution, so that when the fabric is subjected to suitable compressive forces, the fabric will in fact experience compression. Irregular distribution of the water-curable material may prevent uniform compression. A number of water-curable resins including polyurethane, preolymers, and cyanoacrylate esters are well known within the art. Urethanes may be used, due to their elastic memory, such that the urethane will decompress along with the fabric returning to its original size prior to being compressed. The water-curable material has the property that when exposed to water the material is activated by the catalyst and will begin to cure (i.e. harden). The catalyst should be of such a proportion that it causes the cross-linking reaction between the polyurethane prepolymer and the water while not causing the cast to become rigid before the cast is formed on the patient. Preferably, a curing time should be on the order of minutes, thus allowing for the fabric sheet to decompress when saturated with water (e.g. over a period of 1-20 seconds) and allowing sufficient time for a user to wrap the fabric sheet around the limb of the patient prior to the hardening of the resin. The reactivity of the resin can be controlled by proper catalyst selection.

Figure 1C:
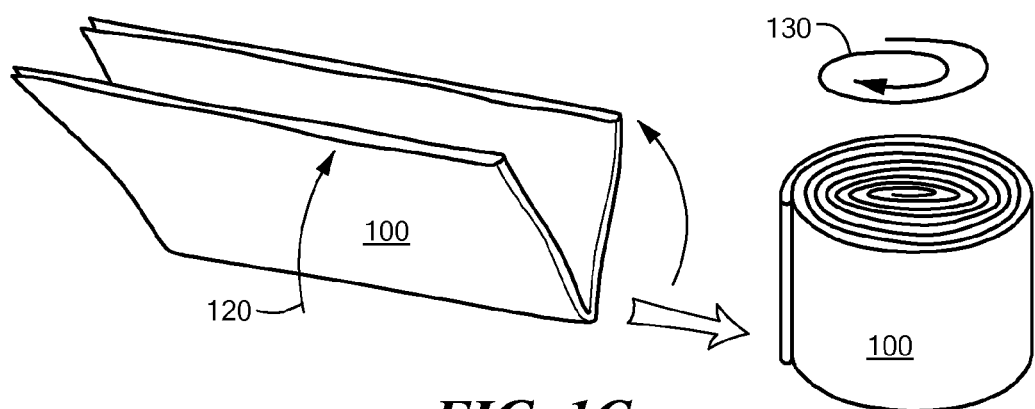
FIG. 1C shows the fabric being folded.

FIG. 1C shows the fabric 100 being folded 120. In certain embodiments, the fabric is folded in half 120 and is rolled 130 to form a cylindrical shape as shown in the figure. The fabric may be folded in other shapes (e.g. square, triangle, or rectangle) or may be folded more than once prior to being compressed. The folding and rolling of the fabric determine the shape of the final compressed article.

Figure 1D:
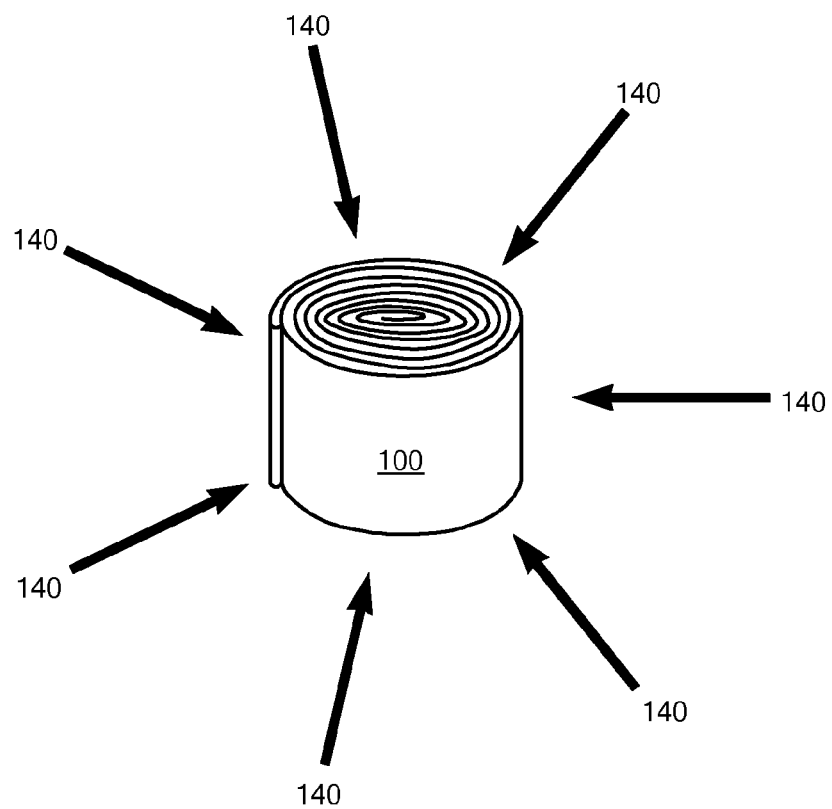
FIG. 1D shows the folded fabric of FIG. 1B after being compressed.

FIG. 1D shows the folded fabric of FIG. 1B after being compressed. Force 140 is applied to all sides of the folded and rolled fabric 100 using a high pressure system (e.g. 1100-1500 $Kg/cm^2$) not shown. High pressure systems for compressing fabrics include model ZMJ-T manufactured by JiaXing ZhiMing Machinery Co. Ltd. The folded and rolled fabric may be placed into a mold within the high pressure machine. The greatest compression of the fabric will be exhibited about the axis with the least resistance or density. Thus, the size of the folded and rolled fabric may compress more about a first axis than about a second axis. The fabric will compress in multiple directions and will exhibit a large change in total surface area. For example, the fabric may originally be a sheet of approximately 30 cm×30 cm with a minimal thickness (0.08 cm) having a surface area of approximately 1800 cm.$^2$ When folded and compressed, the textile has a cylindrical shape that is approximately 2.0 cm in diameter by 1 cm in height with a surface area of approximately 12.56 cm$^2$ Thus, the 30 cm×30 cm sheet is compressed to a coin size that can be readily stored in a medical bag or pocket where the surface area is compressed by an order of approximately 140:1.

Figure 2:
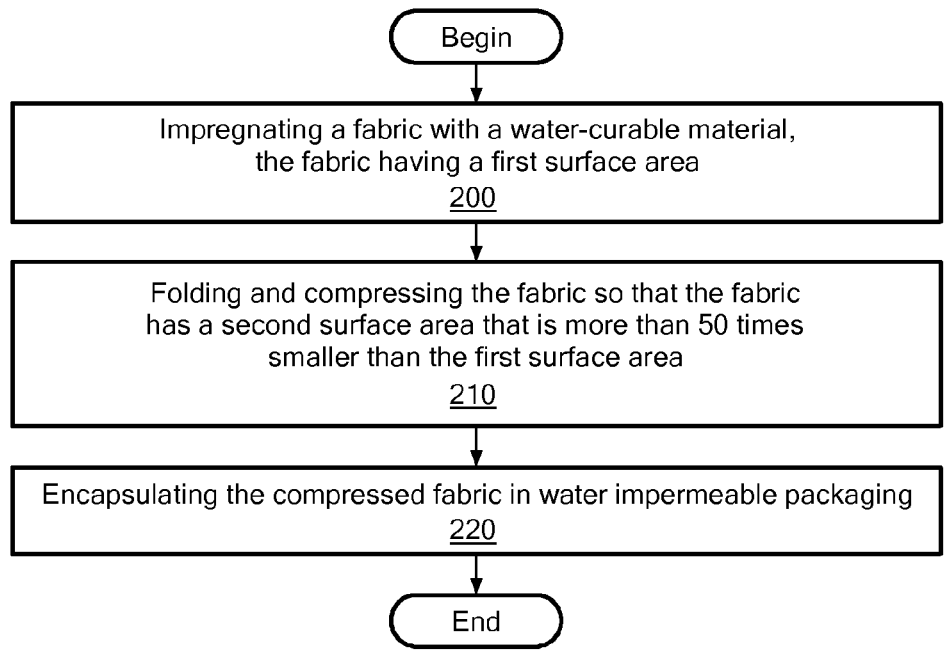
FIG. 2 is a flow chart explaining the creation of the compressed orthopedic cast.

FIG. 2 is a flow chart explaining the creation of a compact package that can be formed into an orthopedic cast when exposed to water. First a fabric is acquired that is formed in a sheet and is sized for use as a cast. For example, the fabric may be formed from natural fibers, such as cotton fibers. In other embodiments of the invention, the fabric may be a man-made fabric, such as viscose. The fabric is preferably made of non-woven fibers, but may also be composed of woven fibers, or a combination thereof. The size of the fabric sheet should preferably be more than 20 cm in length and 20 cm in width, although the sheet may be smaller in size. The preferred size allows for a sheet to be wrapped around a portion of a patient's body. For example, the sheet may be sized to be wrapped around an arm, a leg, or the neck of a patient. The fabric is then impregnated with a water-curable material. 200 As expressed above the water-curable material is preferably sprayed onto the fabric and evenly distributed. Even distribution is preferred so that the fabric will exhibit consistent compression characteristics.

The fabric is then folded and/or rolled into a preferred shape. 210 The shape that the fabric is folded/rolled into is approximately the same shape that the fabric will have after being compressed.

The fabric is then placed into a mold and the mold is inserted into a high pressure machine that compresses the fabric. The fabric is compressed in such a manner that the surface area of the original fabric in sheet form is approximately 50 times or more larger than that of the compressed fabric's surface area.

The compressed fabric is then encapsulated in a water impermeable package. 220. The packaging may be blister packs or other packaging types similar to those used by the pharmaceutical industry to prevent water and water vapor from reaching the contents of the packaging.

Figures 3A, 3B:
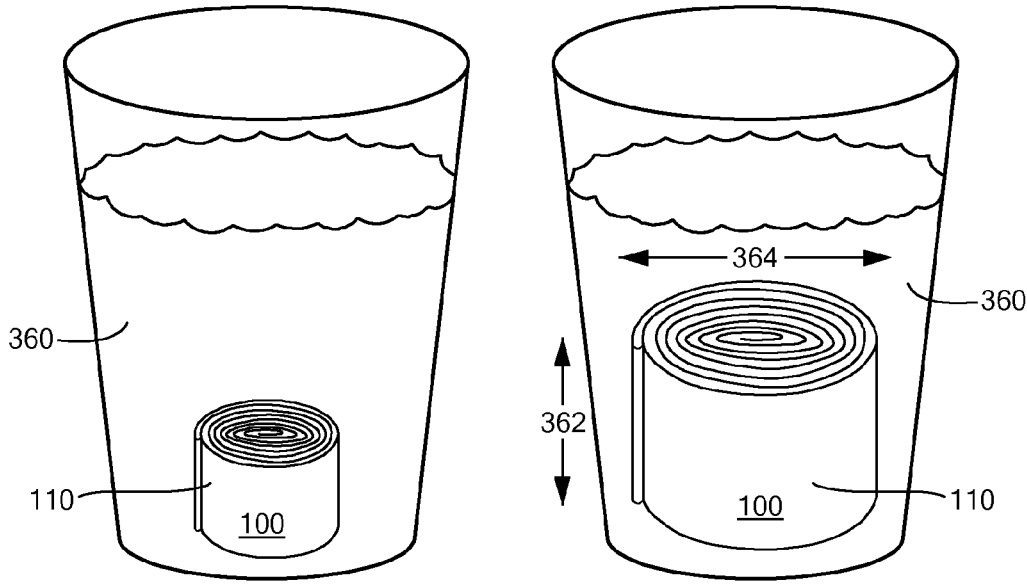
FIG. 3A shows the compressed fabric being placed into a water solution.
FIG. 3B shows the fabric expanding from its compressed state.

FIG. 3A shows the compressed fabric 100 being placed into a water solution 360 after the compressed fabric has been removed from its water-impermeable packaging. The compressed fabric 100 impregnated with the water-curable material 110 may be immersed in water or may be brought into contact with water such that the fabric becomes saturated.

FIG. 3B shows the expansion about multiple directions 362, 364 of the compressed fabric 100 in the presence of water 360. The expansion begins immediately upon contact with the water and full expansion may take approximately 1-20 seconds.

Figure 3C:
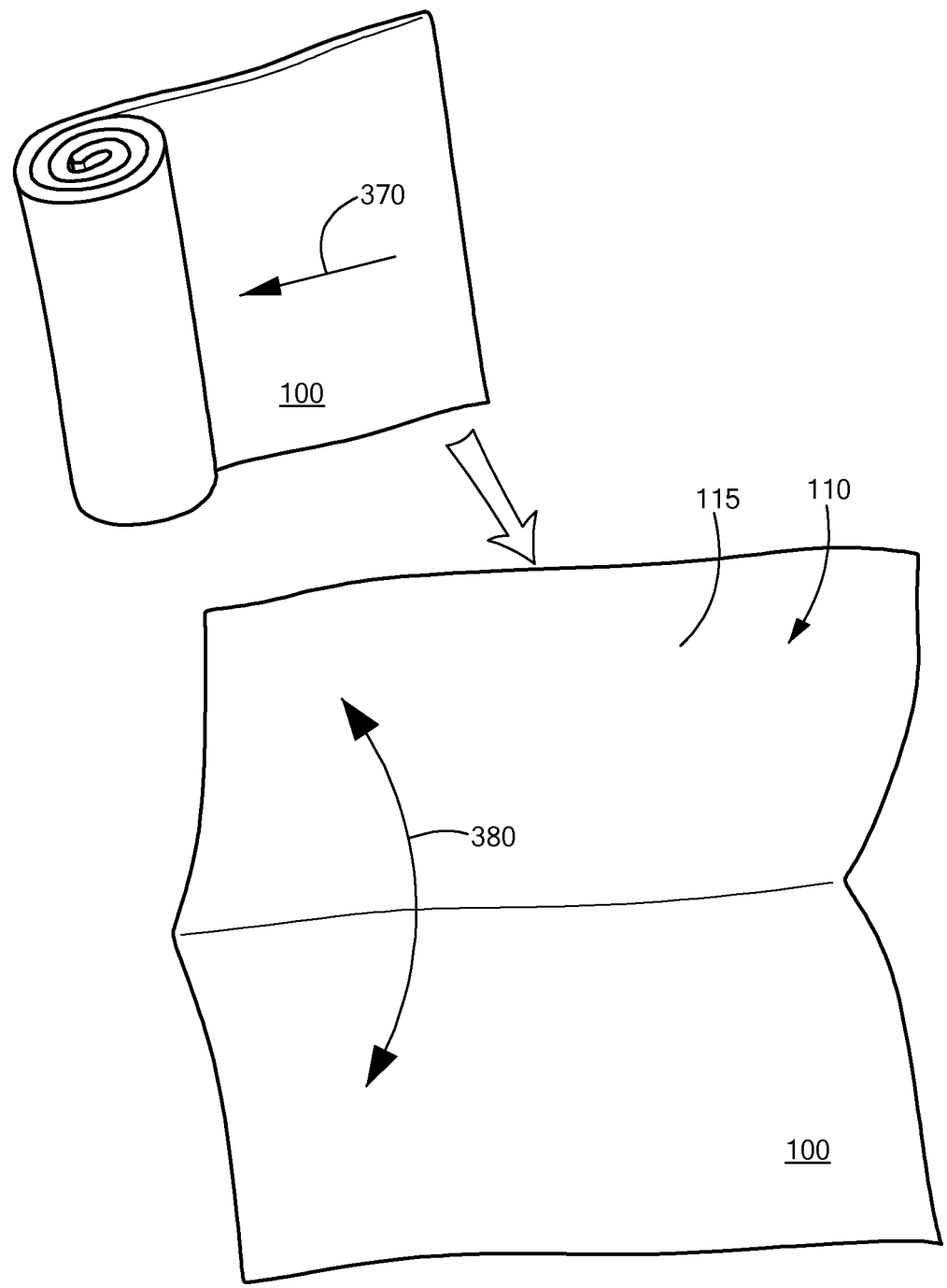
FIG. 3C shows the fabric unfolded forming a sheet.

FIG. 3C shows the expanded fabric 100 being unrolled 370 and unfolded 380 to form a sheet. The fabric 100 is returned substantially to it original size prior to compression and has a surface area that is at least an order of magnitude larger than in its compressed form. At the same time that the compressed fabric is brought into contact with the water, the curing process begins and the catalyst reacts with the water to begin creating a rigid structure from the water-curable material 110 that is present on and within the intersticies 115 of the fabric 100. During the beginning stages of this process the fabric is still malleable and may be placed around a portion of a patient's body. The reactivity of the water-curable material can be controlled by selection of a proper catalyst. The reaction needs to be such that a hard surface does not form immediately, so that the water does not saturate the fabric preventing expansion and also preventing the water from contacting the bulk of the water-curable material. The reactivity also needs to be such that the cast eventually becomes rigid over a long enough period of time to allow for both decompression of the fabric and for the application of the fabric to a patient to form-fit to the limb of the patient that is injured.

In addition to the reactivity, foaming, if it occurs, needs to be controlled. Foaming will occur due to the release of carbon dioxide during a catalytic reaction between water and an isocyanate group. Significant foam will cause the cast have an inconsistent structure and may be prone to failure. As a result the amount of the isocynate group that is present should be balanced, so as to prevent excessive foaming while still providing adequate reactivity so that the process will cause the cast to harden.

Figure 3D:
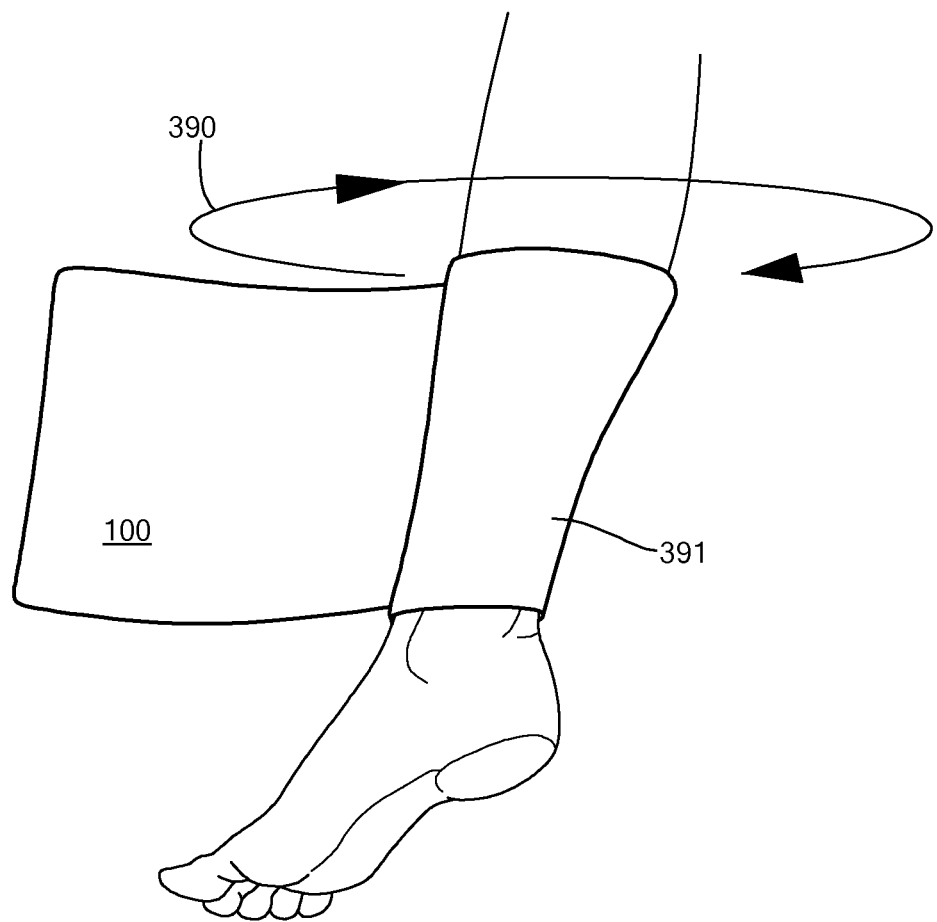
FIG. 3D shows the sheet being placed over a limb of a patient to form a cast.

As shown in the example of FIG. 3D, the fabric 100 is wrapped around 390 the shin 391 of an individual. Multiple sheets of fabric may be used to form-fit the cast around the patient's limb. Preferably, the fabric will significantly overlap when wrapped around the patient so that the cast will form as a continuous surface. After a period of time, the cast will cure and become rigid. The patient may then place weight onto the cast.

Figure 4:
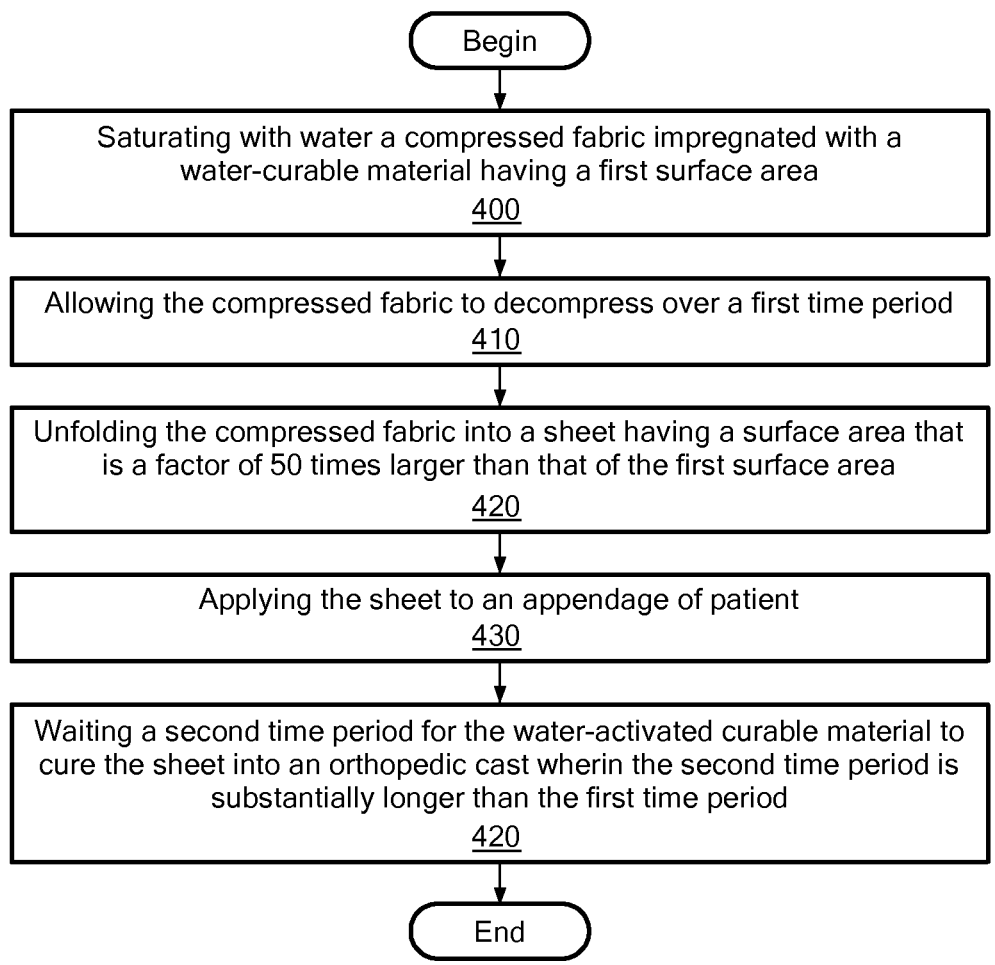
FIG. 4 is a flow chart explaining the use of the compressed object as an orthopedic cast

FIG. 4 is a flow chart explaining the use of the compressed object as an orthopedic cast. Embodiments of the invention may be employed in emergency situations. For example, the compressed orthopedic cast may be useful in wartime situations. An injury to a soldier may occur on the battlefield where the soldier has a broken leg or injured joint and the solider needs to be moved. A medic can unpack the compressed object, and place the object into contact with water in process 400. The water is absorbed into the fibers of the fabric and the fabric begins to decompress in process 410. The compressed fabric expands in all directions, and may expand in one direction to a greater degree than in another, dependant upon the amount of compression that occurred in that direction. The decompression takes a matter of seconds to occur and corresponds to the absorption of the fabric with the water. Thus, the medic waits a first time period for the fabric to decompress in process 420. Once the fabric is decompressed, the medic may unfold the fabric into its original configuration as a sheet. Once unfolded, the compressed fabric has a surface area that is a factor of 50 times or more larger than that of the surface area of the compressed fabric. The medic can then apply the sheet to the appendage of the wounded soldier. The fabric, once expanded, is flexible and can be wrapped around and form-fit to a limb of the injured soldier in process 430. The medic and soldier then wait for the water curable material to cure. The water curable material has an associated setting time, which preferably is on the order of minutes. The setting time is substantially longer than the time period for expansion of the compressed fabric. When the cast is set, the injured appendage is stabilized, and the soldier may then more readily use the appendage with the cast and can be removed from the battlefield.

Although, FIG. 4 is described with respect to a military scenario, it should be recognized that the compressed fabric with water curable material would be appropriate for other environments where injuries may occur that require immediate stabilization of a bone or joint, such as emergency situations, hazardous industrial locations and sporting events. The overall compactness and portability of the compressed object make the casting system ideal for medical kits and use in the field.

In other embodiments, the water curable material may be microinjected into the compressed fabric post compression. One advantage of microinjection is that the amount of the water-curable material (e.g. polyurethane prepolymer) would be reduced due to the decrease in volume of the fabric substrate.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A compact package for making an orthopedic cast, the package comprising:
    a fabric folded and compressed into a coin shape having a height of approximately 1 cm and a diameter of approximately 2 cm, having an initial over-all surface area prior to being saturated with water, that expands to final over-all surface area after saturation with water that is larger by a factor greater than 50 than the initial over-all surface area prior to water saturation in a first period of time;
    a water-curable material, impregnated into the fabric prior to the fabric being folded and compressed, so that when the material is saturated with water, the material cures over a second period of time to become rigid, wherein the second period of time is substantially longer than the first period of time,
    so that for use, the fabric impregnated with the material may be immersed in water and expanded, placed around a portion of a body for which the orthopedic cast is desired, and, after permitting the second period time to elapse, the material has become rigid so as to form the orthopedic cast.

2. The compact package according to claim 1, wherein the fabric is formed from non-woven fibers.

3. The compact package according to claim 2, wherein the non-woven fibers are viscose.

4. The compact package according to claim 1, wherein the water-curable material is a urethane.

5. The compact package according to claim 1, wherein the water-curable material includes polyisocyanate prepolymers.

6. The compact package according to claim 1, wherein second time is less than five minutes.

7. A method of forming an orthopedic cast, the method comprising:
    impregnating a fabric with a water-curable material;
    folding and compressing the fabric containing the water-curable material until the fabric is compressed into a coin having a cylindrical shape and a size of approximately 1 cm in height by 2.0 cm in diameter and has a first surface area;
    saturating with water the compressed fabric impregnated with the water-curable material;
    allowing the compressed fabric to decompress over a first time period;
    unfolding the compressed fabric into a sheet having a final surface area that is a factor of at least 50 times larger than that of the first surface area;
    applying the sheet to an appendage of patient; and
    waiting a second time period for the water-activated curable material to cure the sheet into an orthopedic cast wherein the second time period is substantially longer than the first time period.

8. A method according to claim 7, wherein the compressed fabric is a non-woven material.

9. A method according to claim 8, wherein the non-woven material is cotton.

10. A method according to claim 7, wherein the compressed fabric is viscose.

11. A method according to claim 7, wherein the water-curable material includes polyisocyanate prepolymers.

12. A method according to claim 7, wherein the water curable materials includes polyurethane.

\* \* \* \* \*